United States Patent

Roberts

[11] 4,202,099
[45] May 13, 1980

[54] DENTURE SUPPORT FRAME

[76] Inventor: Ralph Roberts, 920 Rio Dell Ave., Rio Dell, Calif. 95562

[21] Appl. No.: 939,122

[22] Filed: Sep. 5, 1978

[51] Int. Cl.² ............................................. A61C 13/00
[52] U.S. Cl. .................................................... 433/176
[58] Field of Search ........................................ 32/10 A

[56] References Cited

U.S. PATENT DOCUMENTS

| 2,002,048 | 5/1935 | Thomas | 32/5 |
| 4,062,119 | 12/1977 | Linkow | 32/10 A |

*Primary Examiner*—Robert Peshock
*Attorney, Agent, or Firm*—Eugene M. Eckelman

[57] ABSTRACT

A rigid bar arranged to removably support an artificial denture is curved in the shape of the lower jaw bone and has front implant support means as well as rear ramus implant portions. Each of the ramus implant portions includes a tip end of the frame arranged to be inserted in a rearwardly extending opening cut in the jaw bone by the dentist. Such tip ends have laterally extending flattened portions which provide increased bearing support on the jaw bone. The front implant support comprises a depending extension arranged to be inserted in a recess cut in the top surface of the jaw bone, and such extension has a cross blade with one or more forwardly extending tabs arranged to seat on surface portions of the jaw bone. The cross blade may also have rearwardly extending tabs arranged also to seat on surface portions of the jaw bone. The invention further includes the concept of providing partial length rear support bar portions arranged to be implanted at their rear tips in ramus portions of the jaw and arranged to be fastened to a front portion of a support bar.

5 Claims, 10 Drawing Figures

DENTURE SUPPORT FRAME

BACKGROUND OF THE INVENTION

This invention relates to new and useful improvements in denture support frames and is particularly concerned with improvements in such frames for use with lower dentures.

Denture support frames for lower dentures have heretofore been employed which consist of a rigid bar properly sized and shaped to the lower jaw bone. Such a support frame is shown in U.S. Pat. No. 3,641,671. In such patented structure, the rigid bar has rear portions which are implanted in cuts made in the ramus portion of the jaw. A forward intermediate portion of the bar has an integral downward extension arranged to be implanted in a cut made in the jaw bone. Although these implant portions provide a substantially sturdy connection for the denture support bar, the rear tip construction and the front downward extension will in some of the more difficult cases allow undesirable settling of the support bar in the implant areas of the jaw bone.

SUMMARY OF THE INVENTION

According to the present invention and forming a primary objective thereof, means are employed to provide an improved bearing support for implanted portions of denture support frames to increase the bearing area of support and reduce the chances of settling and loosening of the frame.

The structure for carrying out the objectives of the invention includes a rigid bar arranged in a known manner to removably support an artificial denture thereon. This bar is curved to the shape of the jaw bone and has rear ramus implant portions with flattened bearing support means. In addition, a front implanted support for the rigid bar is included and has tabs arranged to seat on the jaw bone surfaces for increasing the area of bearing support on the jaw bone. Rear portions of the bar may be integrally formed with the front portion of the bar or may comprise separate parts arranged to be secured in overlapping engagement with the front portion, thus allowing the rear implant portions to be replaced.

The invention will be better understood and additional objects and advantages will become apparent from the following description taken in connection with the accompanying drawings.

BRIEF DESCRIPTION OF THE DRAWINGS

FIG. 6 is a plan view showing a modified form of the front support of the frame;

DETAILED DESCRIPTION OF PREFERRED EMBODIMENTS

Figure 1:
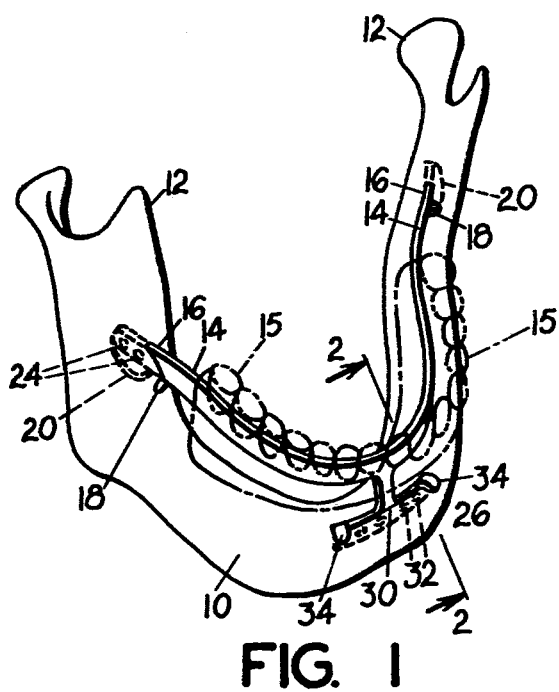
FIG. 1 is a perspective view of a jaw bone having a denture support of the present invention mounted therein, a denture tooth base member being shown in broken lines.
Figure 4:
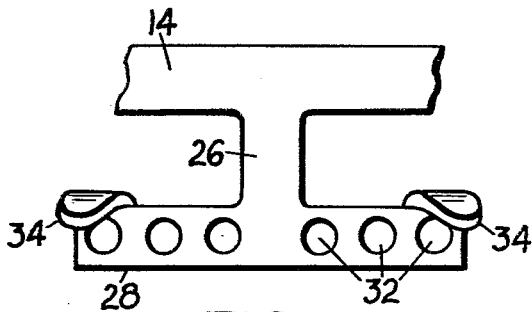
FIG. 4 is an enlarged fragmentary front elevational view taken on the line 4—4 of FIG. 3.

With reference first to FIG. 1, the numeral 10 designates a jaw bone and the numeral 12 designates opposite ramus portions thereof. The denture support frame of the instant invention comprises a rigid bar 14 having its main portion curved to conform to the shape of the jaw bone, such exact shaping and sizing being accomplished by the dentist with suitable tools prior to attachment of the bar in the mouth. The numeral 15 represents a denture member, also seen in FIG. 2, arranged to be supported on the bar 14.

Figure 3:
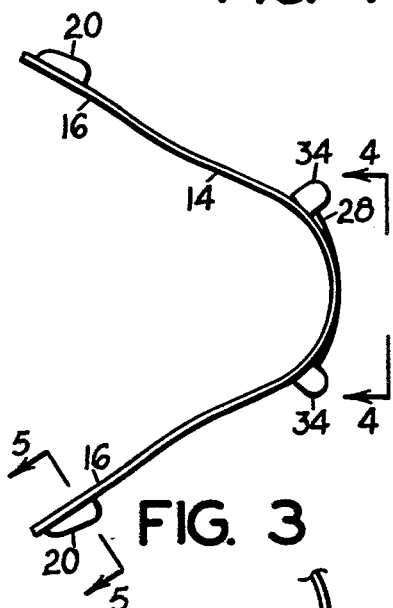
FIG. 3 is a plan view of the denture support frame.
Figure 5:
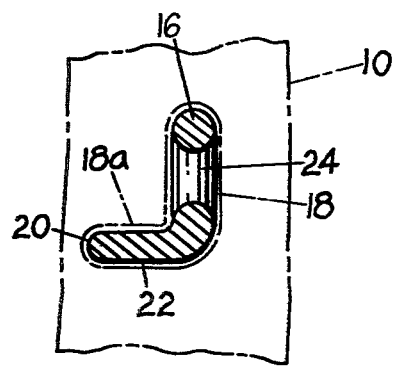
FIG. 5 is an enlarged sectional view taken on the line 5—5 of FIG. 3 and also including in broken lines a portion of the jaw bone and cut-out portions thereof for receiving the present frame.
Figures 8, 9:
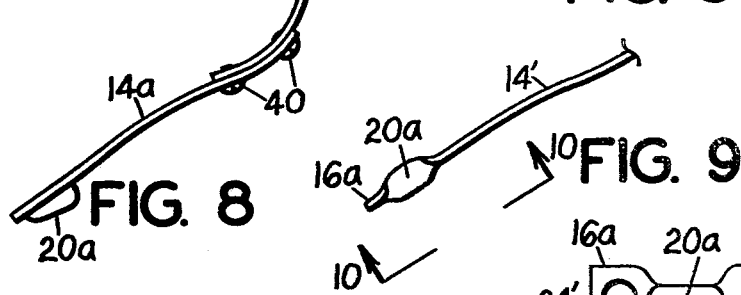
FIG. 8 is a plan view of a two-piece support frame forming a further modification of the invention.
FIG. 9 is a fragmentary plan view of another form of the invention.
Figure 10:
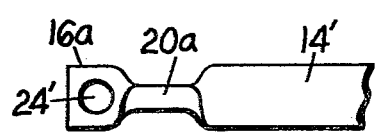
FIG. 10 is an enlarged fragmentary elevational view taken on the line 10—10 of FIG. 9.

The rigid bar 14 has rear terminal or tip ends 16 arranged to be inserted in openings 18 cut by the dentist in the ramus portions of the jaw bone. According to one concept of the invention, the tip ends 16 of the bar 14 have lateral extensions or wings 20 with flat bottom surfaces 22 arranged to fit in lateral extensions 18a of the cuts 18. These extensions increase the bearing support of the bar at the ramus implant portions of the jaw bone and may comprise angular side extensions as shown in FIGS. 1 and 3 or ninety degree twist portions 20a in the bar 14' as shown in FIGS. 9 and 10. The rear tip ends of the bar 14 which are implanted are provided with one or more apertures 24 arranged to receive bone growth therethrough and rigidly anchor these tip ends to the bone. In the embodiment of FIGS. 9 and 10, a portion 16a of the bar 14 extends beyond the twisted portion 20a and this extended portion likewise has one or more holes 24'.

Figure 2:
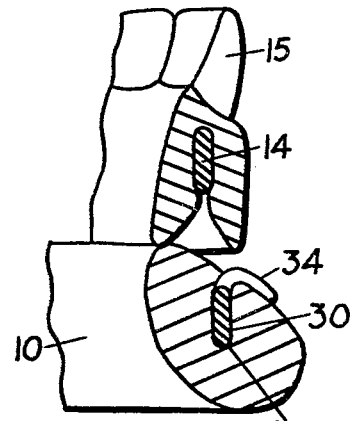
FIG. 2 is an enlarged sectional view taken on the line 2—2 of FIG. 1 and showing the denture tooth base member in full lines.

Bar 14 is provided with a front depending extension 26 having an integral cross blade portion 28 which is substantially parallel with the bar 14 and which is arranged to extend into a recess 30, best seen in FIG. 2, cut in the top surface of the jaw bone by the dentist. The blade portion 28 has a plurality of holes 32 to receive bone growth. The purpose of the blade 28 is to steady the front portion of the bar 14 and also to provide support against downward biting forces of the front teeth. According to the present invention, the bearing support for this portion of the bar is increased by employing one or more forwardly facing tabs 34 which as best seen in FIG. 3 seat on the top surface of the jaw bone 10 forward of the recess 30. These tabs are custom shaped to seat on the top of the jaw bone and generally are rounded so as to conform to the contour of the jaw bone.

Figure 7:
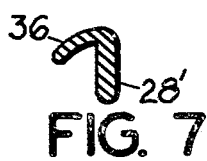
FIG. 7 is an enlarged sectional view taken on the line 7—7 of FIG. 6.

With reference to FIGS. 6 and 7, additional tabs 36 may be provided on the top of blade 28' which extend rearwardly. These tabs, similar to forwardly extending tabs 34', engage the upper surface of the jaw bone for increasing the bearing support area. If necessary the jaw bone is recessed slightly to receive the tabs 36.

FIG. 8 shows an embodiment of the invention having a front bar portion 38 with the same support implant means structure 26 at the front as that shown in FIG. 1 but having replaceable rear bar portions 14a fastened thereto by fasteners 40 such as screws. By means of this structure the segmented structure may be installed from the beginning whereby the rearward portions 14a or forward portion 38 can be replaced if necessary. Also if a one-piece bar 14 has been installed, rearward portions of the bar can be cut off and replacement or auxiliary bars 14a implanted and secured to the front portion of the bar by fasteners 40. In either case it is not necessary to remove the front bar portion if such portion is solidly supported by its implant.

It is to be understood that the forms of my invention herein shown and described are to be taken as preferred examples of the same and that various other changes in the shape, size and arrangement of parts may be resorted to without departing from the spirit of my invention, or the scope of the subjoined claims.

Having thus described my invention, I claim:

1. A denture support frame for lower dentures comprising
   (a) a rigid bar arranged removably to support an artificial denture thereon,
   (b) said bar having front and rear portions and being curved to the shape of the lower jaw bone,
   (c) said bar having rear ramus implant portions,
   (d) and front support means on said bar arranged for engagement with the jaw bone,
   (e) each of said ramus implant portions comprising a tip end,
   (f) at least one of said ramus implant portions at said tip end including a laterally extending flattened portion arranged to be inserted in a correspondingly sized lateral opening cut in the ramus portion of the jaw bone.

2. The denture support frame of claim 1 wherein said tip ends of said ramus implant portions comprise a bar portion arranged to be inserted in a rearwardly extending opening cut in the ramus portion of the jaw bone in communication with the lateral opening cut for said flattened portion.

3. The denture support frame of claim 1 wherein said front support means comprises a depending blade portion arranged to be inserted in a recess cut in a forward top surface of the jaw bone, and forwardly extending rigid tab means on said blade portion arranged to seat on the jaw bone for adding to the supporting area for said front support means.

4. The denture support frame of claim 3 wherein said front support means also includes rearwardly extending rigid tab means on said blade portion arranged to seat on the jaw bone for further adding to the support area for said front support means.

5. The denture support frame of claim 1 wherein said ramus implant portions are a part of a rearward bar portion separate from said front portion and arranged for removable securement to said front portion.

* * * * *